US008696738B2

(12) United States Patent
Noesner et al.

(10) Patent No.: US 8,696,738 B2
(45) Date of Patent: Apr. 15, 2014

(54) COMPOSITE PROSTHESIS WITH EXTERNAL POLYMERIC SUPPORT STRUCTURE AND METHODS OF MANUFACTURING THE SAME

(75) Inventors: Matthew Noesner, West Orange, NJ (US); Jerry Dong, Oakland, NJ (US)

(73) Assignee: MAQUET Cardiovascular LLC, Wayne, NJ (US)

( * ) Notice: Subject to any disclaimer, the term of this patent is extended or adjusted under 35 U.S.C. 154(b) by 283 days.

(21) Appl. No.: 12/784,393

(22) Filed: May 20, 2010

(65) Prior Publication Data
US 2011/0288628 A1    Nov. 24, 2011

(51) Int. Cl.
*A61F 2/06*    (2013.01)
(52) U.S. Cl.
USPC ........................................ 623/1.32
(58) Field of Classification Search
USPC ........ 623/1.32, 1.33, 1.5–1.54; 606/191–194, 606/153, 154, 157, 158
See application file for complete search history.

(56) References Cited

U.S. PATENT DOCUMENTS

| | | | | |
|---|---|---|---|---|
| 3,105,492 | A | * | 10/1963 | Jeckel ............................ 623/1.44 |
| 3,479,670 | A | | 11/1969 | Medell |
| 3,882,845 | A | | 5/1975 | Bucalo |
| 4,306,318 | A | | 12/1981 | Mano et al. |
| RE31,618 | E | * | 7/1984 | Mano et al. .................. 623/1.33 |
| 4,517,687 | A | | 5/1985 | Liebig et al. |
| 4,550,318 | A | | 10/1985 | Prengaman et al. |
| 4,588,461 | A | * | 5/1986 | Braun ............................ 156/143 |
| 4,728,328 | A | * | 3/1988 | Hughes et al. ............. 623/23.69 |
| 4,747,849 | A | * | 5/1988 | Galtier ........................ 623/23.69 |
| 4,850,999 | A | * | 7/1989 | Planck .......................... 623/1.44 |
| 4,973,609 | A | | 11/1990 | Browne |
| 5,061,276 | A | | 10/1991 | Tu et al. |
| 5,116,360 | A | * | 5/1992 | Pinchuk et al. ............. 623/11.11 |
| 5,151,105 | A | * | 9/1992 | Kwan-Gett .................. 623/1.32 |
| 5,152,782 | A | | 10/1992 | Kowligi et al. |
| 5,156,619 | A | | 10/1992 | Ehrenfeld |
| 5,156,620 | A | * | 10/1992 | Pigott .......................... 623/1.25 |
| 5,163,951 | A | | 11/1992 | Pinchuk et al. |
| 5,178,630 | A | | 1/1993 | Schmitt |
| 5,236,447 | A | | 8/1993 | Kubo et al. |
| 5,282,846 | A | | 2/1994 | Schmitt |
| 5,282,848 | A | | 2/1994 | Schmitt |
| 5,385,580 | A | | 1/1995 | Schmitt |

(Continued)

FOREIGN PATENT DOCUMENTS

| | | |
|---|---|---|
| JP | 2000139967 A | 5/2000 |
| JP | 2005505317 A | 2/2005 |
| WO | WO 88/00813 A1 | 2/1988 |
| WO | WO 2005/018502 A1 | 3/2005 |

OTHER PUBLICATIONS

International Search Report and Written Opinion dated Aug. 29, 2011 for PCT/US2011/037183.

(Continued)

*Primary Examiner* — Alvin J. Stewart
(74) *Attorney, Agent, or Firm* — Hoffmann & Baron, LLP (57) ABSTRACT

A prosthesis including a support structure for enhancing kink and/or crush resistance. The support structure is connected to an outer surface of the prosthesis and includes at least two components, one of which has a lower melting point than the other. The component with the lower melting point is used to connect the support structure to the outer surface of the prosthesis.

31 Claims, 3 Drawing Sheets

(56) References Cited

U.S. PATENT DOCUMENTS

| | | | |
|---|---|---|---|
| 5,413,598 A | 5/1995 | Moreland | |
| 5,443,499 A | 8/1995 | Schmitt | |
| 5,476,506 A | 12/1995 | Lunn | |
| 5,487,858 A | 1/1996 | Schmitt | |
| 5,496,364 A | 3/1996 | Schmitt | |
| 5,509,931 A | 4/1996 | Schmitt | |
| 5,527,353 A | 6/1996 | Schmitt | |
| 5,554,180 A * | 9/1996 | Turk | 623/1.25 |
| 5,556,426 A * | 9/1996 | Popadiuk et al. | 623/1.33 |
| 5,584,877 A | 12/1996 | Miyake et al. | |
| 5,607,478 A | 3/1997 | Lentz et al. | |
| 5,609,624 A * | 3/1997 | Kalis | 623/1.32 |
| 5,629,077 A * | 5/1997 | Turnlund et al. | 623/1.15 |
| 5,665,114 A | 9/1997 | Weadock et al. | |
| 5,697,969 A | 12/1997 | Schmitt et al. | |
| 5,716,394 A | 2/1998 | Bruchman et al. | |
| 5,735,897 A * | 4/1998 | Buirge | 623/1.15 |
| 5,749,880 A * | 5/1998 | Banas et al. | 606/198 |
| 5,800,510 A | 9/1998 | Schmitt | |
| 5,800,512 A | 9/1998 | Lentz et al. | |
| 5,800,514 A | 9/1998 | Nunez et al. | |
| 5,824,047 A | 10/1998 | Moreland | |
| 5,824,050 A | 10/1998 | Karwoski et al. | |
| 5,824,054 A | 10/1998 | Khosravi et al. | |
| 5,861,033 A | 1/1999 | Martakos et al. | |
| 5,871,537 A * | 2/1999 | Holman et al. | 623/1.23 |
| 5,910,168 A | 6/1999 | Myers et al. | |
| 5,911,753 A | 6/1999 | Schmitt | |
| 5,976,192 A * | 11/1999 | McIntyre et al. | 600/36 |
| 5,990,378 A * | 11/1999 | Ellis | 623/11.11 |
| 5,993,489 A * | 11/1999 | Lewis et al. | 623/1.13 |
| 6,001,125 A | 12/1999 | Golds et al. | |
| 6,036,724 A | 3/2000 | Lentz et al. | |
| 6,039,755 A | 3/2000 | Edwin et al. | |
| 6,053,938 A | 4/2000 | Goldmann et al. | |
| 6,053,943 A * | 4/2000 | Edwin et al. | 623/1.25 |
| 6,080,198 A * | 6/2000 | Lentz et al. | 128/898 |
| 6,096,070 A | 8/2000 | Ragheb et al. | |
| 6,099,557 A | 8/2000 | Schmitt | |
| 6,117,535 A | 9/2000 | Szycher et al. | |
| 6,136,022 A | 10/2000 | Nunez et al. | |
| 6,176,874 B1 | 1/2001 | Vacanti et al. | |
| 6,187,038 B1 | 2/2001 | Sullivan et al. | |
| 6,197,051 B1 | 3/2001 | Zhong | |
| 6,221,101 B1 | 4/2001 | Harris et al. | |
| 6,273,912 B1 | 8/2001 | Scholz et al. | |
| 6,273,917 B1 * | 8/2001 | Inoue | 623/23.64 |
| 6,287,337 B1 | 9/2001 | Martakos et al. | |
| 6,312,462 B1 * | 11/2001 | McDermott et al. | 623/1.25 |
| 6,319,279 B1 | 11/2001 | Shannon et al. | |
| 6,344,052 B1 | 2/2002 | Greenan et al. | |
| 6,355,063 B1 * | 3/2002 | Calcote | 623/1.42 |
| 6,371,981 B1 | 4/2002 | Yang et al. | |
| 6,371,982 B2 | 4/2002 | Berg et al. | |
| 6,497,710 B2 | 12/2002 | Yencho et al. | |
| 6,511,491 B2 | 1/2003 | Grudem et al. | |
| 6,540,773 B2 | 4/2003 | Dong | |
| 6,547,820 B1 | 4/2003 | Staudenmeier | |
| 6,554,855 B1 | 4/2003 | Dong | |
| 6,569,191 B1 * | 5/2003 | Hogan | 623/1.11 |
| 6,585,762 B1 | 7/2003 | Stanish | |
| 6,589,468 B1 | 7/2003 | Schmitt | |
| 6,689,160 B1 | 2/2004 | Okuda et al. | |
| 6,692,523 B2 * | 2/2004 | Holman et al. | 623/1.25 |
| 6,706,064 B1 * | 3/2004 | Anson | 623/1.25 |
| 6,716,239 B2 | 4/2004 | Sowinski et al. | |
| 6,719,783 B2 | 4/2004 | Lentz et al. | |
| 6,723,121 B1 | 4/2004 | Zhong | |
| 6,746,480 B2 | 6/2004 | Scholz et al. | |
| 6,773,457 B2 | 8/2004 | Ivancev et al. | |
| 6,774,278 B1 | 8/2004 | Ragheb et al. | |
| 6,814,753 B2 | 11/2004 | Schmitt | |
| 6,821,295 B1 | 11/2004 | Farrar | |
| 6,827,735 B2 * | 12/2004 | Greenberg | 623/1.25 |
| 6,887,270 B2 | 5/2005 | Miller et al. | |
| 6,890,546 B2 | 5/2005 | Mollison et al. | |
| 6,893,457 B2 | 5/2005 | Dong | |
| 6,899,728 B1 | 5/2005 | Phillips et al. | |
| 6,939,372 B2 | 9/2005 | Dong | |
| 6,966,918 B1 | 11/2005 | Schuldt-Hempe et al. | |
| 6,991,637 B2 | 1/2006 | Crawley et al. | |
| 6,994,666 B2 * | 2/2006 | Shannon et al. | 600/16 |
| 6,994,724 B2 | 2/2006 | Schmitt | |
| 7,018,388 B2 | 3/2006 | Yencho et al. | |
| 7,060,023 B2 | 6/2006 | French et al. | |
| 7,081,129 B2 * | 7/2006 | Chobotov | 623/1.13 |
| 7,108,715 B2 * | 9/2006 | Lawrence-Brown et al. | 623/1.21 |
| 7,150,758 B2 * | 12/2006 | Kari et al. | 623/1.25 |
| 7,198,638 B2 | 4/2007 | Dong | |
| 7,224,271 B2 | 5/2007 | Wang | |
| 7,279,175 B2 | 10/2007 | Chen et al. | |
| 7,297,158 B2 | 11/2007 | Jensen | |
| 7,326,244 B2 | 2/2008 | Drasler et al. | |
| 7,364,587 B2 | 4/2008 | Dong et al. | |
| RE40,404 E * | 6/2008 | Schmitt et al. | 623/1.51 |
| 7,396,363 B2 * | 7/2008 | Frid | 623/1.15 |
| 7,402,174 B2 | 7/2008 | Dong | |
| 7,452,374 B2 * | 11/2008 | Hain et al. | 623/1.44 |
| 7,491,230 B2 * | 2/2009 | Holman et al. | 623/1.25 |
| 7,510,571 B2 | 3/2009 | Spiridigliozzi et al. | |
| 7,524,335 B2 | 4/2009 | Slivka et al. | |
| 7,524,445 B2 | 4/2009 | Duran et al. | |
| 7,530,996 B2 | 5/2009 | Bentele et al. | |
| 7,560,006 B2 | 7/2009 | Rakos et al. | |
| 7,615,071 B2 * | 11/2009 | Chobotov | 623/1.13 |
| 7,659,219 B2 * | 2/2010 | Biran et al. | 442/401 |
| 7,699,887 B2 * | 4/2010 | Burnside et al. | 623/1.38 |
| 7,718,556 B2 * | 5/2010 | Matsuda et al. | 442/123 |
| 7,799,068 B2 * | 9/2010 | Holman et al. | 623/1.25 |
| 7,803,178 B2 * | 9/2010 | Whirley et al. | 623/1.13 |
| 7,879,085 B2 * | 2/2011 | Sowinski et al. | 623/1.28 |
| 7,963,988 B2 * | 6/2011 | Peckham et al. | 623/1.29 |
| 7,993,391 B2 * | 8/2011 | Stinson | 623/1.44 |
| 8,083,806 B2 * | 12/2011 | Shalaby et al. | 623/23.66 |
| 8,128,982 B2 * | 3/2012 | Neary | 427/2.24 |
| 2002/0111668 A1 * | 8/2002 | Smith | 623/1.13 |
| 2003/0125796 A1 * | 7/2003 | Dong | 623/1.13 |
| 2003/0139806 A1 | 7/2003 | Haverkost | |
| 2004/0176836 A1 * | 9/2004 | Kari et al. | 623/1.32 |
| 2004/0199246 A1 * | 10/2004 | Chu et al. | 623/1.32 |
| 2006/0058867 A1 * | 3/2006 | Thistle et al. | 623/1.13 |
| 2006/0264138 A1 | 11/2006 | Sowinski et al. | |
| 2007/0135890 A1 | 6/2007 | Dong | |
| 2009/0138068 A1 * | 5/2009 | West et al. | 623/1.13 |

OTHER PUBLICATIONS

International Search Report and Written Opinion for PCT/US2011/037183, mailed Aug. 29, 2011.
Office Action for Japanese Patent Application No. 2013-511360.

\* cited by examiner

COMPOSITE PROSTHESIS WITH EXTERNAL POLYMERIC SUPPORT STRUCTURE AND METHODS OF MANUFACTURING THE SAME

FIELD OF THE INVENTION

The present invention relates generally to an implantable device. More particularly, the present invention relates to a prosthesis, such as a graft, including a support structure providing, e.g., enhanced kink and/or crush resistance.

BACKGROUND OF THE INVENTION

Implantable devices are commonly used in medical applications. One of the more common device structures includes tubular prostheses, which may be used as vascular grafts to replace or repair damaged or diseased blood vessels. To maximize the effectiveness of such a prosthesis, it should be designed with characteristics which closely resemble that of the natural body lumen which it is repairing or replacing.

One form of a conventional tubular prosthesis specifically used for vascular grafts includes a textile tubular structure formed by weaving, knitting or braiding synthetic fibers into a tubular configuration. Tubular textile structures have the advantage of being naturally porous, which allows desired tissue ingrowth and assimilation into the body. This porosity, which allows for ingrowth of surrounding tissue, must be balanced with fluid tightness so as to minimize leakage during the initial implantation stage. Other tubular prosthesis are formed of expanded polytetrafluoroethylene (ePTFE), which may be used for smaller diameter prosthesis.

Composite ePTFE textile grafts are also known. For example, U.S. Patent Publication No. 2003/0139806 describes an inner layer of ePTFE and an outer layer of textile material bonded together by an elastomeric bonding agent to form a vascular prosthesis.

It is known to provide enhanced kink and crush resistance properties to ePTFE grafts by directly attaching a spirally wrapped polymeric coil or support element made of PTFE. The ePTFE graft is heated to a temperature sufficient to assure that the PTFE coil bonds to the graft outer surface. This method, however, does not necessarily work well for composite grafts where the material of the wrapped support structure is made from a substantially different material from the underlying graft material. For example, when the underlying graft has a textile surface, attempting to attach a wrapped PTFE support member through conventional melting methods would likely weaken the textile layer because the melting temperature of PTFE (327° C.) is substantially higher than the melting temperature range of conventional implantable textiles, such as Dacron® (polyethylenetherephthalate, 240-258° C.). This holds true for other externally wrapped support structures, which have a melting temperature range above that of the underlying graft body.

Joining of very different materials to form an integrated assembly has many challenges associated with the physical and chemical differences of the materials. For example, in some instances, a wrapped support structure is intended to be attached in a manner which prevents it from being removed without damaging the underlying graft. In other cases, a wrapped support structure must be attached in a manner sufficient to perform its kink and crush resistance role, but allow for removal without damaging the underlying graft body. Such a removable support structure would allow the physician to tailor the graft to the patient, without risk of loss of structural integrity of the overall graft structure. Differences in such inherent properties as melting temperatures, surface properties, molecular weights, biocompatibility, flexibility, solubility, as well as elongation moduli, are some of the contributing factors which make it difficult to join dissimilar polymeric structures together to make an implantable prosthesis having crush and kink resistance.

Therefore, there is a need for a composite graft that can be securably attached to a coil or other external support element without compromising the graft, and which overcomes the difficulties associated with joining dissimilar materials.

SUMMARY OF THE INVENTION

An example embodiment of the present invention provides an implantable prosthesis which includes: (a) a generally tubular body including an outer textile surface; and (b) a support structure attached to the outer textile surface of the body and configured to increase at least one of the kink and crush resistance of the body. The support structure includes a first component and a second component. The second component (i) including a polymeric material, (ii) having a lower melting temperature than that of the first component and the body, and (iii) connecting the first component to the body.

According to an example embodiment, the body of the implantable prosthesis may include an inner layer made from a biocompatible polymer.

According to an example embodiment, the outer textile surface may include the outer surface of an outer textile layer including filaments or yarns with interstices or pores between them. The second component extends into the interstices or pores and thereby mechanically connects the first component of the support structure to the outer textile layer.

According to an example embodiment, the outer textile layer includes a knit, weave or braid pattern of the filaments or yarns and wherein the second component of the support structure is removably connected to the outer textile layer such that removal of the first component does not substantially damage the pattern. The textile pattern of the invention may be chosen from any useful pattern, including but not limited to knits, weaves, braids, or other spun fiber constructions.

According to an example embodiment, the support structure may be configured such that removal of the first component from the outer textile layer removes a portion of the second component while leaving a remainder of the second component connected to the outer textile layer.

According to an example embodiment, a biocompatible elastomeric bonding agent bonds an outer surface of the inner layer to an inner surface of the outer textile layer.

According to an example embodiment, the first component has a melting temperature of approximately 130° C.-170° C. and the second component has a melting temperature of approximately 60° C.-105° C.

According to an example embodiment, the first component is made from polypropylene.

According to an example embodiment, the second component is made from polyethylene.

According to an example embodiment, the support structure is wrapped about the outer textile surface. Various forms of wrapping may be used, including helical wrapping.

According to an example embodiment, the inner layer is made from at least one of ePTFE, polyurethane, silicone, and an acrylate. Combinations of biocompatible polymers may also be used.

According to an example embodiment, the inner layer is made from ePTFE.

According to an example embodiment, the second component is disposed about the first component. Desirably, the first component is a core component and the second component is a layer or sheath that partially or completely covers the core.

According to an example embodiment, there is provided an implantable prosthesis which includes: (a) a generally tubular body which includes an inner biocompatible layer (referred to as a luminal or blood-contacting layer), and an outer textile layer disposed about the inner biocompatible layer; and (b) a support structure attached to the outer textile layer and configured to increase at least one of the kink and crush resistance of the body, the support structure including a bead or coil having a core component and an outer sheath component surrounding the core component, the outer sheath component being a polymer having a melting temperature lower than the melting temperature of the core component and lower than the melting temperature of the body. Desirably, the core component is also a polymer component. The support structure may be formed by coating the core component with the sheath component or by co-extrusion techniques.

A method of preparing an implantable prosthesis according to an example embodiment of the present invention includes: (a) applying a support structure to an outer textile surface of a generally tubular body of the prosthesis, the support structure including a first component and a second component disposed about the first component, the second component being polymeric and having a lower melting temperature than that of the first component and the body; and (b) melting the second component, and not the first component or the body, so as to cause the second component to connect the first component to the body.

According to an example embodiment, the method further includes the preliminary steps of forming the body by disposing a textile outer layer over a biocompatible polymeric inner layer and connecting the outer and inner layers using a biocompatible elastomeric bonding agent.

A method of implanting a prosthesis into a subject according to an example embodiment of the present invention includes the steps of: (a) determining an appropriate size of the prosthesis for the subject, the prosthesis including a generally tubular body and a support structure attached to an outer surface of the body and configured to increase at least one of the kink and crush resistance of the body, the support structure including a first component and a second component, the second component having a lower melting temperature than that of the first component and the body, the second component connecting the first component to the body; (b) removing the first component from at least one end of the prosthesis consistent with the appropriate size while leaving the support structure connected along a remainder of the body; and (c) implanting the prosthesis in the subject.

Combinations of any of the aforementioned example embodiments are included as part of the invention.

DETAILED DESCRIPTION OF PREFERRED EMBODIMENTS

Figure 1:
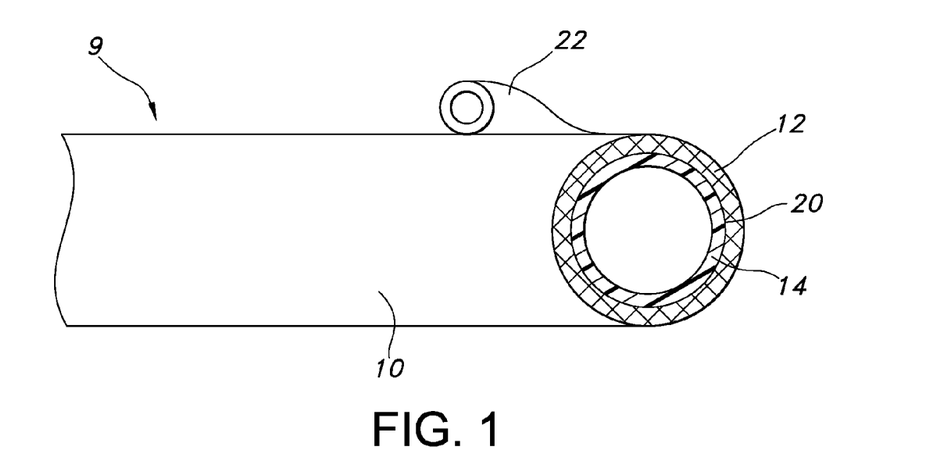
FIG. 1 is a perspective view of a prosthesis according to an example embodiment of the present invention shown in partial cross section.

FIG. 1 shows a prosthesis 10 according to an example embodiment of the present invention. The prosthesis 10 may be generally tubular, and includes a composite implantable prosthesis having an inner layer 14, e.g., a tube made from a biocompatible polymer, and an outer layer 12, e.g., a tubular textile layer, at least partially disposed about the inner layer 14. The prosthesis 10 may have any desired thickness, e.g., 0.1 mm to about 2 mm, the thickness being measured from the outer surface of the device to the inner surface.

As detailed further below, the two layers 12, 14 may be joined, e.g., using a bonding agent, and supported by a support structure 22. The support structure 22 includes a first material and a second material disposed on the first material and having a lower melting point than the first material. This novel support structure allows the graft to be heated to a temperature sufficient to assure bonding of the support structure to the graft without compromising the graft.

Composite Prosthesis

Inner layer 14 may be made from of a biocompatible material, such as a biocompatible polymer, e.g., ePTFE, polyurethane, acrylates, silicones and copolymers and combinations thereof. In one embodiment, the inner layer 14 is made from at least one of ePTFE, polyurethane, silicone, and an acrylate.

Outer textile layer 12 may be formed from a biocompatible material having at least one different property than inner layer 14. For example, outer textile layer 12 may be a textile formed from yarns that may be flat, shaped, twisted, textured, preshrunk or un-shrunk. The yarns may be natural or synthetic, e.g., thermoplastic materials including, but not limited to, polyesters, polypropylenes, polyethylenes, polyurethanes, polynaphthalenes, polytetrafluoroethylenes, expanded polytetrafluoroethylene, and the like. The yarns may be of the multifilament, monofilament or spun types. Multifilament yarns offer increased flexibility. Monofilament yarns are useful for enhanced crush resistance.

As used herein, the term "PTFE" refers to polytetrafluoroethylene, and refers to any structure made at least partially of polytetrafluoroethylene. The term "ePTFE" refers to expanded polytetrafluoroethylene, and refers to any structure made at least partially of expanded polytetrafluoroethylene.

The inner layer 14 may be produced from the expansion of PTFE formed, e.g., in a paste extrusion process. The PTFE extrusion may be expanded and sintered in a manner well known in the art to form ePTFE having a microporous structure defined by nodes interconnected by elongate fibrils. The distance between the nodes, referred to as the internodal distance (IND), may be varied by the parameters employed during the expansion and sintering process. The resulting process of expansion and sintering yields pores within the structure of the inner layer 14. The size of the pores are defined by the IND of the inner layer 14.

The outer textile layer 12 may be designed as a tissue contacting surface in order to promote enhanced cellular ingrowth, which may contribute to the long term patency of the prosthesis. The inner layer 14 may be used as a blood contacting surface so as to minimize leakage and to provide a generally anti-thrombogetic surface. In certain situations, the layers may be reversed where indicated.

The inner layer 14 and the outer textile layer 12 may be bonded to each other, e.g., using a bonding agent 20. The bonding agent may be applied as a solution to an outer surface of the inner layer 14 or to an inner surface of the outer textile layer 12 by a spray coating process. However, other known processes may be employed to apply the bonding agent 20.

The bonding agent 20 may include, for example, various biocompatible, elastomeric bonding agents such as urethanes, polycarbonate urethanes, styrene/isobutylene/styrene block copolymers (SIBS), silicones, and combinations thereof. Other similar materials are contemplated. Most desirably, the bonding agent may include polycarbonate urethanes sold under the trade name CORETHANE® by Boston Scientific Corporation, Natick, Mass. This urethane is provided as an adhesive solution with preferably 7.5% Corethane, 2.5 W30, in dimethylacetamide (DMAc) solvent.

For inner layers 14 made from ePTFE, a highly hydrophobic material, it is useful to use a elastomeric bonding agent 20, which makes it way into the micropores of the ePFTE structure, enhanced bonding. One example of a class of bonding agent with elastic properties are those formed from the reaction of alphatic macroglycols and aromatic or aliphatic diisocyanates.

Monofilament Biocompatible Polymeric Support Structure

Figure 2:
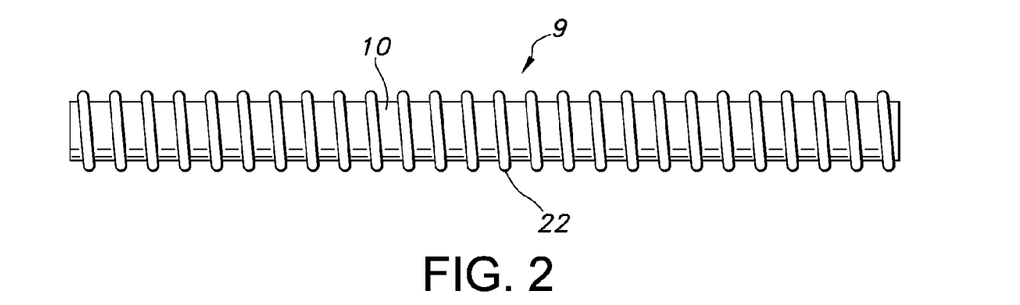
FIG. 2 is a side view of the prosthesis of FIG. 1.
Figure 3:
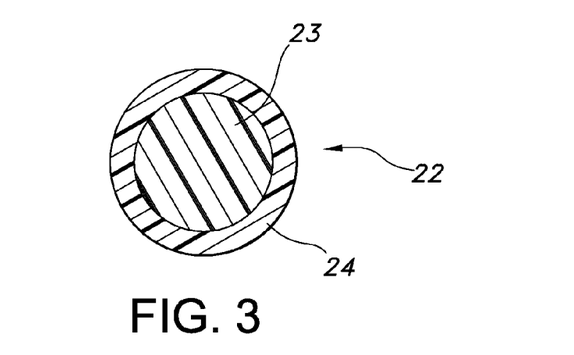
FIG. 3 is a cross-sectional view of the support structure of FIG. 1.
Figure 4:
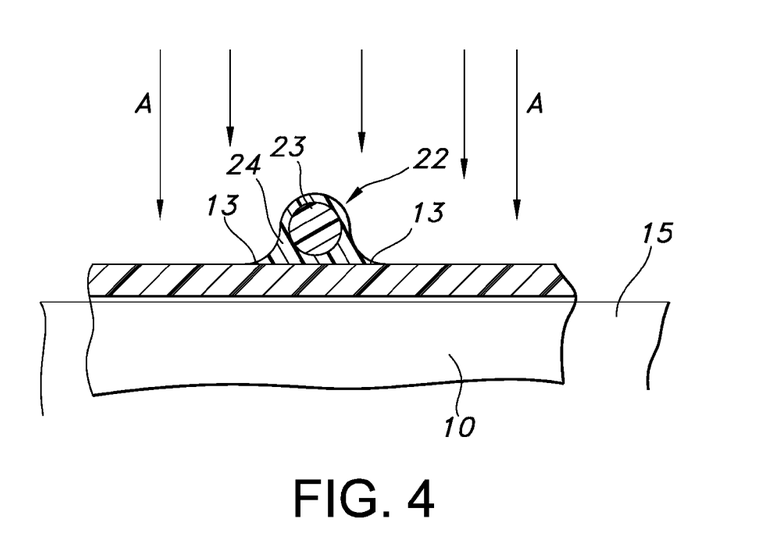
FIG. 4 is a side view of the prosthesis of FIG. 1 with the support structure and outer textile layer shown in cross section.

With reference to FIGS. 2-4, the prosthesis 10 is wrapped with a support structure 22 in order to enhance crush and/or kink resistance. The support structure 22 may extend along the entire length of the prosthesis 10 or just along select portions, e.g., those requiring additional support. The support structure 22 may be produced separately from the prosthesis layers, e.g., by casting or extrusion.

The support structure 22 may include materials having different melting temperatures. As illustrated, support structure 22 has a first component 23 at least partially surrounded by a second component 24 which has a lower melting point than that of the first component 23. The second component 24 is at least partially disposed about the first component 24. The first component 23 and second component 24 may be coextruded. The second component 24 need not entirely surround the first component 23 prior to connection to the body 10 so long as second component 24, upon melting and subsequently cooling, extends through interstices or pores in the outer textile layer 12 of the prosthesis 10 and also wraps around the first component 23 sufficient to create a hold on the first component 23. The support structure 22 may have a core first component 23 surrounded by a sheath second component 24.

The second component 24 is made from a material, desirably a polymeric material, having a lower melting point than the first component 23. For example, the second component 24 may include a polyethylene polymer, and the first component 23 may include a polypropylene polymer. This permits the prosthesis 10 to be heated to a melting temperature high enough to melt the second component 24 of the support structure 22, such that it may flow into interstices or pores of the textile layer 12 of the prosthesis 10, but not high enough to melt the first component 23 of the support structure 22 or the inner layer 14 and outer textile layer 12 of the prosthesis 10. Thus, the second component 24 connects the first component 23 to the prosthesis 10.

The support structure 22 may have any cross-sectional configuration. The cross section of the support structure 22 may be selected so as to maximize the surface area through which it may be fused to the outer textile layer 12 of the prosthesis 10. The cross section of the support structure 22 may also be selected, e.g., a semicircle or half moon, so as to, minimize the external irregularity or roughness of the prosthesis 10 by limiting the height of the support 22 above the outer textile layer 12.

The overall size and geometry of the support structure 22 are adaptable depending on the material used and the desired end properties of the prosthesis 10.

The support structure 22 may be attached to the outer textile layer 12 such that it is removable or non-removable, as further discussed herein. In one embodiment, the physician can remove or unravel the support structure 22 from the outer textile layer 12 in order to size or tailor the prosthesis 10 to the patient.

In another embodiment, the support structure 22 may be heated at a temperature, e.g., above 160° C., sufficient to cause both the first component 23 (i.e., the core) and the second component 24 (i.e., the sheath) to melt. If the polymeric support structure is not adequately disposed about or wrapped around the prosthesis, then it will simply melt off the surface of the prosthesis. However, if the polymeric support structure is contained during the melting process, then both polymers will flow into the outer textile layer 12 of the prosthesis 10 and flatten-down, or in some cases be recessed, to achieve a low profile allowing, e.g., for the use of a smaller diameter delivery mechanism. In some embodiments, the total profile will essentially be the same as or only nominally above the profile of the underlying prosthesis 10.

In another embodiment, the support structure 22 may be applied to only a section of the base of the prosthesis 10, for example, leaving the ends either unsupported or supported with a removable polymeric support to create a prosthesis that is customizable. The customizable ends will allow the physician to cut the prosthesis 10 to the appropriate length and still make the necessary sutures for implantation.

In an example embodiment, the first component 23, e.g., made from polypropylene, has a melting point which is about 130° C.-170° C. and the second component 24, e.g., made from polyethylene, has a melting point of about is 60° C.-105° C.

As shown in FIG. 2, prosthesis 10 has a polymeric support structure 22 wrapped helically around the prosthesis 10 and connected thereto. The polymeric support structure 22 of the prosthesis 10 as shown is a monofilament, but may be a braid of two or more, e.g., smaller, filaments. Alternatively, the polymeric support structure may be composed of two or more filaments wrapped independently about the outer textile layer 12. Each filament may be composed of a single monofilament or may be composed of an arrangement of two or more filaments mutually intertwined, e.g., in a regular braid or twist pattern.

The support structure 22 may be comprised of a single filament length wrapped helically around the tube for the length of the outer textile layer 12. Alternatively, one or more support structures may extend longitudinally along a length of the prosthesis 10. Further, the filament component may be discontinuous, being comprised of more than one segment of filament wrapped or otherwise arranged along the outer textile layer 12. If more than one segment is employed, the segments may be wrapped sequentially, so that the ends of each segment are juxtaposed with each adjacent segment end and attaching each segment to the outer textile layer 12 so that segment ends are as close to each other in the longitudinal dimension as possible. Arrangements in which such segments are not matched in helical and/or longitudinal position are also contemplated as an embodiment of the invention. Alternatively, when more than one filament segment is used, the segments may overlap longitudinally such that two or more segments, whether of identical or non-identical lengths and/ or diameters, may be fused to the outer textile layer 12 at any plane along the length of the prosthesis 10.

In an example embodiment, the support structure 22 may be wrapped around the outer textile layer 12, e.g., at an angle of winding, relative to the axis, of from about 30° to about less than 90°.

In an example embodiment with more than one support structure wrapped about the outer textile layer 12, the angle of winding of each the support structures 22 may be equal to that of the others so that the support structures 22 are substantially mutually parallel, i.e., non-overlapping.

In another embodiment, the support structure 22 may be wrapped under tension against the outer textile layer 12 of the prosthesis 10 and may be heated to a temperature sufficient to melt the second component 24 of the support structure 22. The heating is conducted such that the second component 24 flows into and removably adheres to the outer textile layer 12 of the prosthesis 10 while also remaining sufficiently disposed about first component 23. Second component 24 cools on first component 23 and is configured about first component 23 in a manner allowing it to physically hold onto first component 23 and resist up to a predetermined level of pulling force separating first component 23 from outer textile layer 12, e.g., 10 grams to 300 grams. The connection between the second component 24 of the support structure 22 and the outer textile layer 12 of the prosthesis 10 is strong enough to withstand such predetermined pulling force and remains intact, thus preserving the integrity of the outer textile layer 12 of the prosthesis 10, even upon removal of first component 23 from the prosthesis 10 (although removal of the first component 23 may take a portion of the second component 24 of the support structure 22 with it). After heating, a removable support structure 22 is created. This permits the physician with the option of customizing the supported length to suit his/her needs and provide an area that is capable of being sutured.

In another embodiment, the support structure 22 may be wrapped under tension against the outer textile layer 12, and may be heated to a temperature to melt both the first component 23 and the second component 24 and compressed against the second component 24 of the prosthesis 10 to effectuate a non-removable adherence to the prosthesis 10. After heating, a low profile non-removable support is created.

In another embodiment, if the ends of the prosthesis 10 are completely unsupported or supported with a removable polymeric support material, it will create a prosthesis with a support structure that is customizable. The customizable ends will allow the physician to cut the prosthesis 10 to the appropriate length and still be able to make the necessary sutures.

The support structure 22 may be wrapped around the outer textile layer 12 while under tension, otherwise the support structure 22 might slip and/or be displaced during manipulation prior to sintering. The tension level is sufficient to avoid slippage while low enough to avoid damage to the support structure 22. The compression may be applied by a flexible tubular wrap or sheath. The flexible tubular wrap or sheath may be a shrink wrap silicone, or a textile wrap designed to tightly fit about the structure.

In one embodiment, the support structure 22 may be melted to the tubular outer textile layer 12 of the prosthesis. This allows the formation of a support structure 22 integrated with the prosthesis 10 without requiring additional means for causing the tubing and the polymeric support components to adhere to one another. The outer textile layer 12 may be made from a textile, e.g., woven or knit, including overlapping or interconnecting filaments or yarns forming interstices between the filament or yarns. The second component 24 of the support structure 22 extends into the interstices and thereby mechanically connects the first component 23 of the support structure 22 to the outer textile layer 12.

Accordingly, adhesives, laminates or other physical means for maintaining the integrity of the composite prosthesis are rendered unnecessary, thus simplifying the structure of the prosthesis 10 and the method of its manufacture.

In another embodiment, the support structure 22 may be adhered or otherwise bonded to the prosthesis 10. The material of the second component 24 of the support structure 22 may be adapted or chosen specifically to ensure an excellent bond with the outer textile layer 12 of the prosthesis while the first component 23 may be chosen to assure ideal physical support properties for the prosthesis.

In another embodiment, the support structure 22 may be melted to the outer textile layer 12 of the prosthesis 10 substantially continuously or discontinuously along the length of the prosthesis 10.

In an example embodiment, the support structure 22 may be in the form of a bead and may be configured to be flat, square, or ribbon-like spherical elliptical or other shapes.

Methods of Assembly

Having described the prosthesis 10 of the present invention, an example method of manufacturing the prosthesis 10 in accordance with the present invention may now be described.

Generally, the prosthesis 10 is formed from an inner layer 14, an outer textile layer 12 at least partially disposed about the inner layer 14 and joined thereto by a bonding agent 20. A support structure 22, made up of core material 23 and second component 24, is applied to the outer textile layer 12. The second component 24 is melted onto the outer textile layer 12 to thereby adhere the support structure 22 to the prosthesis 10. The support structure 22 may be melted, for example, by application of heat at a temperature sufficient to melt the second component 24 but not the first component 23 (or core) of the support structure 22.

The inner layer 14 of prosthesis 10 may be formed in a conventional forming process such as by tubular extrusion or by sheet extrusion where the sheet is formed into a tubular configuration. The inner layer 14 is placed over a stainless steel mandrel and the ends of the tube are secured. The prosthesis is then spray coated with an adhesive solution of anywhere from 1%-15% Corethane® urethane, 2.5 W30 in DMAc. As noted above, other adhesive solutions may also be employed. The coated inner layer 2 may be dried at room temperature. Alternatively, it may be placed in an oven heated in a range from 18° C. to 150° C. oven for 5 minutes to overnight to dry off the solution. If desired, the spray coating and drying process can be repeated multiple times to add more adhesive to the inner layer 14. The inner layer 14 is then covered with the outer textile layer 12 to form the composite prosthesis 10. One or more layers of resilient sheath, is then placed over the composite structure to hold the composite structure together and assure that complete contact and adequate pressure is maintained for bonding purposes. The assembly of the composite prosthesis within the sheath is placed in an oven and heated in a range of 180°-220° C. for approximately 5-30 minutes to bond the layers together.

One technique used to attach the support structure 22 to the outer textile layer 12 is shown in FIG. 4. In this example, prosthesis 10 is a graft composed of multiple layers including textile and ePTFE and has joined thereto, e.g., in a helical fashion therearound, a two-layer support structure 22. In order to join the support structure 22 to the prosthesis 10, the prosthesis 10 is placed over a solid mandrel 15. Conventional external heating, e.g., by a convection oven, (arrows A), is applied to the support structure 22 positioned over the prosthesis 10. While this is adequate to bond the support structure 22 to the outer layer 12, heating in this manner may cause the second component 24 of the support structure to uncontrollably flow and create fillets 13 at the juncture of the support structure 22 and the outer textile layer 12 of the prosthesis 10 thereby forming a tent configuration between the outer textile layer 12 and the support structure 22. This method of attachment via conventional external heating, as indicated by arrows A, results in a reduced peel strength of attachment that is undesirable and further causes an area of reduced flexibility due to the larger and thicker fillet areas formed by the melted polymer. While composite prostheses of the present invention formed in this manner results in a higher degree of crushed and kink resistance, the composite structure may lose flexibility which is desirable in an implantable prosthesis. Also, as noted there may be a tendency for the support structure to lose certain of its peel strength of attachment.

Figure 5:
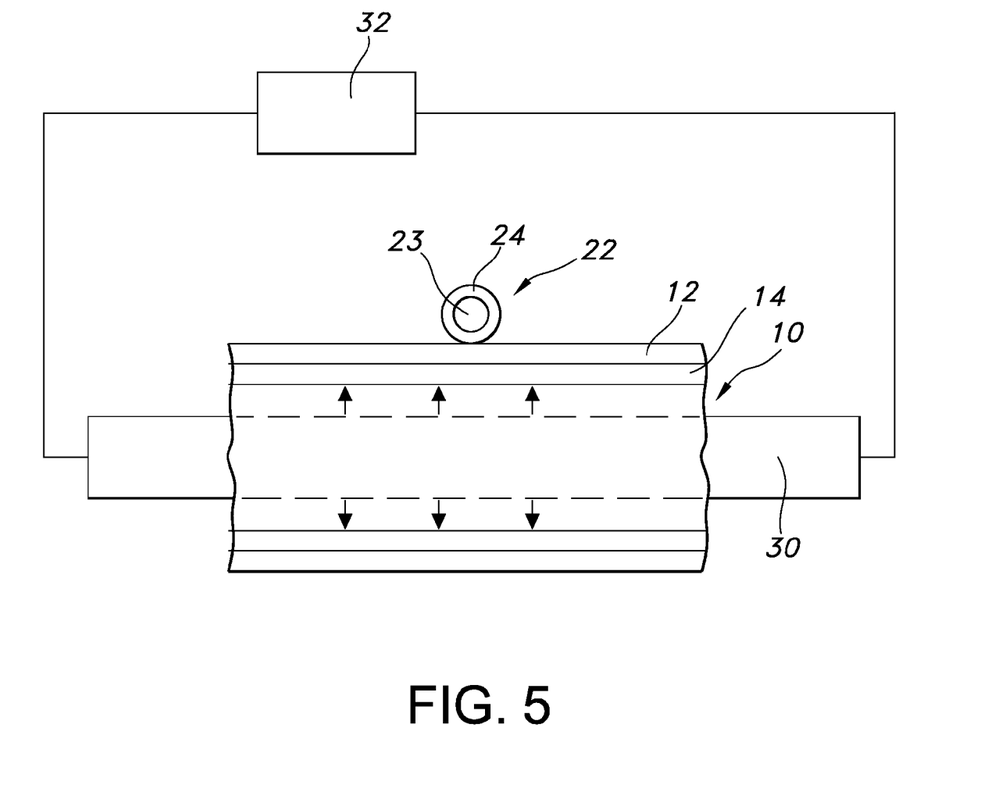
FIG. 5 is a schematic representation of an example of a mechanism used to assemble the prosthesis of FIG. 1.

Referring now to FIG. 5, another technique for connecting the support structure 22 to the prosthesis 10 is described. The prosthesis 10 having support structure 22, e.g., coiled therearound, is placed on a mandrel 30, e.g., made from 316 stainless steel tubing. The mandrel 30 is heated from within the prosthesis 10 to effectuate melting of the support structure 22 to the prosthesis 10. The heat is transferred in the direction of arrows B from the mandrel 30 to the prosthesis 10. The mandrel may be heated in a wide variety of manners. The mandrel may be heated by applying heated fluids, such as liquid or high temperature granular solids such that the composite prosthesis is melted by raising the temperature of the support structure 22 above its melting point.

In accordance with one embodiment of the present invention, a heated circulating bath 32 of, e.g., fluid or granular solids, is heated to approximately above the melting point of at least the second region 24 of the support structure 22, e.g., above about 60-105° C. A pump (not shown) circulates the heated material through the mandrel 30. The heat from the material passing through the mandrel 30 is transferred through the wall of the mandrel (arrow B) and into the surface of the outer textile layer 12 of the prosthesis 10 sufficient to melt at least the second component 24 of the support surface 22.

A pump (not shown) in the heater bath 32 circulates the heated material through the mandrel 30 and back into the bath 32. The heat from the material passing through the mandrel 30 is transferred through a wall of the mandrel and through the prosthesis. The prosthesis is held in this state for enough time to melt just the second component 24, e.g., made from polyethylene, of the support structure 22 in contact with the outer textile layer 12 of the prosthesis, e.g., made from ePTFE.

Attachment of the support structure 22 may also be effectuated by applying pressure, with or without heat, to compress the support structure 22 against the outer textile layer 12 to produce a low profile structure. The pressure may be applied, e.g., using a flexible wrapper sheath. The flexible wrapper sheath may be formed, e.g., from a textile or polymer.

It is also contemplated that the present technique could be used to cool products which require low temperature cycle. Alternatively, after heating the composite prosthesis the mandrel can be used to inject low temperature fluid into the line to rapidly cool the product. Temperature control or changes may be used to temper or anneal products to create various polymer microstructures for various performance criteria.

The attachment process described in FIG. 5 may also be used with different support structures, for example, those made from a single material or multiple materials and wrapped in different configurations as well.

Figure 6:
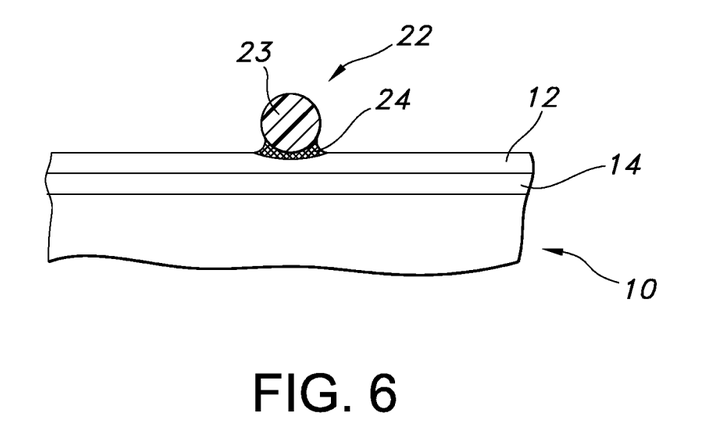
FIG. 6 is a side view and partial cross section of an example embodiment of the present invention.

Use of a support structure 22 having a first component 23 with a melting point greater than the melting point of the second component 24 allows the appropriate amount of heat to be applied so that only the second component 24 melts, i.e., the heat applied is above the melting point of the second component 24, but lower than the melting point of the first component 23. The result of such melting is shown in FIG. 6. As can be seen, heat applied from within the prosthesis 10 effectuates melting of the outer layer material 24 such that it cools on the bottom of the inner layer material 23, i.e., where the support structure 22 contacts the outer textile layer 12 of the prosthesis, and may partially reside or soak into the outer textile layer 12, e.g., extending into interstices in the knit or woven structure of the outer textile layer 12, serving to connect the first component 23 to the prosthesis 10. The connection is strong enough to keep the support structure in place along the prosthesis 10 during use in a patient's body but also allows the support structure 22 to safely be pulled off the outer textile layer 12, e.g., along the ends of the prosthesis 10 so as to allow sizing before implantation, without substantial damage to the, e.g., knit or woven pattern, of the outer textile layer 12. The connection may be configured such that removal of the first component 23 from the outer textile layer 12 removes a portion of the second component 24, while leaving a remainder of the second component 24 connected to the outer textile layer 12.

Figure 7:
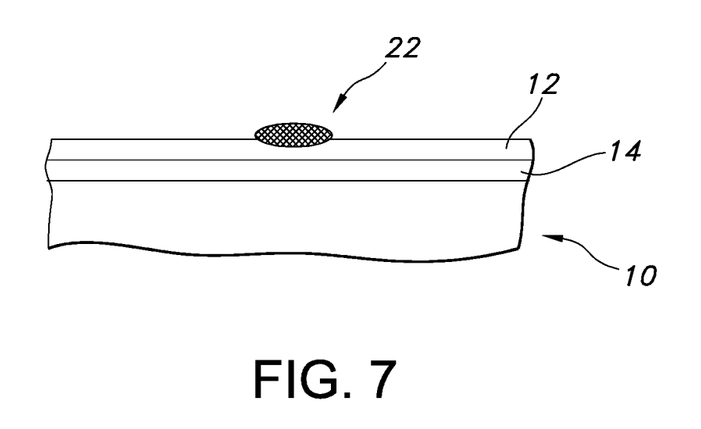
FIG. 7 is a side view and partial cross section of an example embodiment of the present invention.

According to another example method for making the prosthesis 10, the end product of which is shown in FIG. 7, melting is performed at a temperature above the melting point of both the first component 23 and the second component 24. In such an embodiment, the entire support structure 22 is at least partially melted and allowed to soak into and bond to the outer textile layer 12, which provides for a non-removable lower profile support structure.

According to another example method for making the prosthesis 10, this time a composite prosthesis structure having a ePTFE inner layer and a textile outer layer, the prosthesis is placed on a stainless steel mandrel and has a barium sulfate-containing polypropylene/polyethylene bicomponent monofilament support structure wrapped about it under tension. The barium sulfate is a radiopaque material and allows for visualization under fluoroscopy by the physician.

This sub-assembly is placed in a laboratory convection oven at 140° C. for 8 minutes. After the oven cycle, and once the prosthesis is cool, it can be removed from the mandrel. The result is a prosthesis with a traditional bead support structure that is radiopaque and removable to customize.

According to another example method of making prosthesis 10, the prosthesis 10 is covered by a silicone tube, a layer of knit material, a second layer of silicone tube, and a PTFE tape wrap. The silicone-knit-silicone-PTFE covering is used to apply pressure to the prosthesis during the heating cycle. After heating the prosthesis at 170° C. for 8 minutes in a laboratory convection oven, the silicone-knit-silicone-PTFE covering is removed and discarded. The result is a prosthesis with a low profile, non-removable, radiopaque, support wrap that is melted into the outer layer of the prosthesis.

According to another embodiment of the invention, there is provided a method of implanting a prosthesis 10 into a subject according to an example embodiment of the present invention. The method includes the steps of: (a) determining an appropriate size of the prosthesis 10 for a subject, the prosthesis 10 including a generally tubular body and a support structure 22 attached to an outer surface of the body and configured to increase at least one of the kink and crush resistance of the body, the support structure 22 including a first component 23 and a second component 24, the second component 24 having a lower melting temperature than that of the first component 23 and the body, the second component 24 connecting the first component 23 to the body; (b) removing the first component 23 from at least one end of the prosthesis 10 consistent with the appropriate size while leaving the support structure 22 connected along a remainder of the body; and (c) implanting the prosthesis 10 in the subject.

Various changes to the foregoing described and shown structures would now be evident to those skilled in the art. Accordingly, the particularly disclosed scope of the invention is set forth in the following claims.

What is claimed is:

1. An implantable prosthesis comprising:
    (a) a generally tubular body comprising an outer textile surface; and
    (b) a support structure attached to the outer textile surface of the body and configured to increase at least one of kink resistance and crush resistance of the body, the support structure comprising: a first component; and a second component, the second component (i) comprising a polymeric material, (ii) having a lower melting temperature than that of the first component and the body, and (iii) connecting the first component to the body; and wherein prior to implantation a portion of the first component and a portion of the second component are removable with respect to the outer textile surface without substantially compromising the structural integrity of the outer textile surface upon removal.

2. The implantable prosthesis of claim 1, wherein the body of the implantable prosthesis comprises an inner layer made from a biocompatible polymer.

3. The implantable prosthesis of claim 2, wherein a portion of the support structure is configured to be removably attached to the outer textile layer such that removal of the portion of the first component relative to the outer textile layer removes portion of the second component while leaving a remainder of the second component connected to the outer textile layer.

4. The implantable prosthesis of claim 2, wherein a biocompatible elastomeric bonding agent bonds an outer surface of the inner layer to an inner surface of an outer textile layer.

5. The implantable prosthesis of claim 2, wherein the inner layer is made from at least one of ePTFE, polyurethane, silicone, and an acrylate.

6. The implantable prosthesis of claim 2, wherein the inner layer is made from ePTFE.

7. The implantable prosthesis of claim 1, wherein the outer textile surface is an outer surface of an outer textile layer comprising filaments or yarns with interstices or pores between them, wherein the second component extends into the interstices or pores and thereby mechanically connects the first component of the support structure to the outer textile layer such that connection between the support structure and the body is sufficiently strong to secure the support structure to the outer textile surface when the prosthesis is positioned in a patient's body but also allows a portion of the support structure to be safely pulled off the outer textile surface so as to allow for sizing of the prosthesis or customizing a location of the support structure before implantation.

8. The implantable prosthesis of claim 7, wherein the outer textile layer comprises a knit, woven or braid pattern of the filaments or yarns and wherein the second component of the support structure is removably connected to the outer textile layer such that removal of the first component does not substantially damage the knit, woven or braid pattern.

9. The implantable prosthesis of claim 1, wherein the first component has a melting temperature of approximately 130° C.-170° C. and the second component has a melting temperature of approximately 60° C.-105° C.

10. The implantable prosthesis of claim 1, wherein the first component is made from polypropylene.

11. The implantable prosthesis of claim 1, wherein the second component is made from polyethylene.

12. The implantable prosthesis of claim 1, wherein the support structure is wrapped about the outer textile surface.

13. The implantable prosthesis of claim 1 wherein the second component is disposed about the first component.

14. The implantable prosthesis of claim 1, wherein the first component is co-extruded with the second component so as to be continuous with the second component.

15. The implantable prosthesis of claim 1, wherein the support structure is directly attached to the outer textile surface such that the second component is positioned between and connects the first component to the body.

16. The implantable prosthesis of claim 1, wherein the first component forms a core of the support structure and the second component at least partially encases the first component forming a complete or partial sheath around the first component.

17. An implantable prosthesis comprising:
    a generally tubular body having a generally tubular configuration when inserted into a subject during implantation, wherein the body comprises an outer textile surface; and a support structure disposed about the body, wherein the support structure comprises: a first polymer component; and a second polymer component secured to the first polymer component such that a portion of the second polymer component is in intimate contact with and located about a portion of the first polymer component thereby connecting the first polymer component to the body, wherein the second polymer component is different from the first polymeric component; and wherein prior to implantation the portion of the first polymer component and the portion of the second polymer component are detachable with respect to the outer textile surface so as to be capable of being pulled off along a length of the outer textile surface without substantially damaging the outer textile surface and so as to facilitate cutting the prosthesis to a desired length or customizing a location of the support structure.

18. The implantable prosthesis of claim 17, wherein the second polymer component has a lower melting point than a melting point of the first polymer component and a melting point of the body.

19. The implantable prosthesis of claim 17, wherein the first polymer component forms a core of the support structure and the second polymer component at least partially encases the first polymer component forming a complete or partial sheath around the first polymer component.

20. An implantable prosthesis comprising: a generally tubular body comprising an outer textile surface; and a support structure configured to increase at least one of kink resistance and crush resistance of the body, wherein the support structure comprises: a first component; and a second component connecting the first component to the body, wherein the second component comprises a polymeric material; and wherein prior to implantation a portion of the support structure is safely detachable with respect to the outer textile surface such that a portion of the first component and a portion of the second component can be safely pulled off the outer textile surface so as to facilitate cutting the prosthesis to a desired length or customizing a location of the support structure.

21. The implantable prosthesis of claim 17, wherein the support structure is directly connected to the outer textile surface.

22. The implantable prosthesis of claim 17, wherein the first polymer component is polypropylene and wherein the second polymer component is polyethylene.

23. The implantable prosthesis of claim 20, wherein removal of the portion of the support structure does not substantially damage the outer textile surface.

24. The implantable prosthesis of claim 20, wherein the second component has a lower melting point than a melting point of the first component and a melting point of the body.

25. The implantable prosthesis of claim 20, wherein removal of the portion of the support structure does not substantially damage the outer textile surface and wherein removal of the portion of the first component relative to the outer textile surface removes the portion of the second component while leaving a remainder portion of the second component connected to the outer textile surface.

26. The implantable prosthesis of claim 25, wherein the remainder portion of the second component is capable of withstanding a predetermined pulling force of 10 grams to 300 grams.

27. The implantable prosthesis of claim 20, wherein the first component forms a core of the support structure and the second component is configured as a sheath encasing the first component.

28. The implantable prosthesis of claim 20, wherein the support structure is configured as a composite polymer bead and wherein the first component comprises a polymer material different than the polymer material of the second component.

29. The implantable prosthesis of claim 20, wherein an end of the body is unsupported by the support structure.

30. The implantable prosthesis of claim 20, wherein the support member is disposed about and directly attached to the body without any additional means for attaching the support member to the body.

31. The implantable prosthesis of claim 20, wherein the body has a generally tubular configuration when inserted into a subject during implantation.

* * * * *